United States Patent

Tsuda et al.

Patent Number: 5,380,455
Date of Patent: Jan. 10, 1995

[54] DETERGENT COMPOSITION

[75] Inventors: Hiroko Tsuda, Tokyo; Akira Shigeta, Hasaki; Hidenobu Koyanagi, Yono, all of Japan

[73] Assignee: Kao Corporation, Tokyo, Japan

[21] Appl. No.: 67,790

[22] Filed: May 27, 1993

[30] Foreign Application Priority Data

Jun. 1, 1992 [JP] Japan .................... 4-140549

[51] Int. Cl.⁶ .................. C11D 3/37; C11D 3/18; C11D 3/20
[52] U.S. Cl. .................. 252/174.23; 252/171; 252/172; 252/174.15; 252/174.17; 252/174.21; 252/174.24; 252/DIG. 2; 252/DIG. 5; 252/DIG. 13; 252/DIG. 14
[58] Field of Search .......... 252/174.23, 174.24, 252/DIG. 2, DIG. 5, DIG. 13; 424/70

[56] References Cited

U.S. PATENT DOCUMENTS

| | | | |
|---|---|---|---|
| 3,378,609 | 4/1968 | Fasick et al. | 524/520 |
| 3,920,389 | 11/1975 | Eanzel | 252/8.6 |
| 3,920,614 | 11/1975 | Kirimoto et al. | 252/305 |
| 3,959,462 | 5/1976 | Parks et al. | 252/DIG. 2 |
| 3,960,797 | 6/1976 | Inman | 428/421 |
| 4,792,444 | 12/1988 | Fukasawa et al. | |

*Primary Examiner*—Paul Lieberman
*Assistant Examiner*—A. E. Hertzog
*Attorney, Agent, or Firm*—Oblon, Spivak, McClelland, Maier & Neustadt

[57] ABSTRACT

A detergent composition which comprises the following components (A) and (B):

(A) a fluorine-containing polymer having a perfluoroalkyl group and an alkyl group in the molecule, and
(B) a liquid oil base.

The present detergent composition is capable of quickly and effectively removing not only ordinary make-up cosmetics but also fluorine-containing cosmetics which are difficult to be removed by conventional detergent compositions.

14 Claims, No Drawings

DETERGENT COMPOSITION

BACKGROUND OF THE INVENTION

1. Field of the Invention

The present invention relates to a detergent composition which exhibits excellent detergency particularly against make-up cosmetics and dirts on the skin and the hair.

2. Description of the Background Art

There are cleansing cosmetic preparations, massage cosmetic preparations and the like for applying oil components to the skin with a view toward removing the dirt or make-up cosmetics on the skin or massaging the skin. These cosmetics are applied to the skin, extended thereon, and finally removed from the skin. As such cosmetics, oil-like products, creams of an oil-in-water type or water-in-oil type emulsion, or gels of an oil-in-surfactant type emulsion have been on the market.

In the meantime, current make-up cosmetics contain fluorine-treated powders, oils of fluorine-series and the like in addition to conventional oil components, with an aim to enhance the durability of the cosmetics against sebum and perspiration. These functionally improved cosmetics are hardly removed completely by conventional cleansing oils, creams and gels, and it is necessary to use a physical force which, however, generally proves insufficient removal in spite of labor consumed. Furthermore, conventional cleansing compositions are accompanied by a drawback where the dirts once separated from the surface of the skin are apt to re-deposit on the skin when the cleansing compositions are washed away. This is because the conventional cleansing compositions do not have ability of stably dispersing and emulsifying the dirts containing oils of fluorine series or the like. To avoid such a drawback, one may propose the incorporation of oils of fluorine series per se into cleansing compositions relying on their good compatibility with fluorine-containing cosmetics. This, however, presents other problems in that oils of fluorine series are expensive, and they have a poor compatibility with other oil components of the cleansing composition, which indicates difficulty in the formulation of the composition.

SUMMARY OF THE INVENTION

In view of the foregoing circumstances, the present inventors have carried out an extensive investigation with a view toward solving the above-described problems. As a result, it has been found that when an liquid oil is incorporated together with a polymer which contains a fluorine atom (hereinafter referred to as fluorine-containing polymer) having a perfluoroalkyl group and an alkyl group into a detergent composition, the obtained detergent composition can easily and successfully release not only sebum and ordinary make-up cosmetics but also fluorine-containing make-up cosmetics from the surface of the skin and the hair, and the composition has an excellent storage stability. In an aspect of the present invention, there is thus provided a detergent composition which comprises the following components (A) and (B):

(A) a fluorine-containing polymer having a perfluoroalkyl group and an alkyl group in the molecule, and
(B) a liquid oil base.

In another aspect of the present invention, there is also provided a detergent composition which comprises the following components (A) through (C):

(A) a fluorine-containing polymer having a perfluoroalkyl group and an alkyl group in the molecule,
(B) a liquid oil base, and
(C) a surfactant.

In further aspect of the present invention, there is also provided a detergent composition which comprises the following components (A) through (D):

(A) a fluorine-containing polymer having a perfluoroalkyl group and an alkyl group in the molecule,
(B) a liquid oil base,
(C) a surfactant, and
(D) a water-soluble compound having a hydroxyl group.

The above and other objects, features and advantages of the present invention will be readily appreciated from the preferred embodiments of the present invention, which will be described subsequently in detail.

DETAILED DESCRIPTION OF THE INVENTION AND PREFERRED EMBODIMENTS

According to the present invention, detergent compositions having excellent detergency against not only sebum and ordinary make-up components but also fluorine-containing components of make-up cosmetics, and having excellent storage stability are obtained.

The fluorine-containing polymer of the component (A) useful in the practice of this invention has a perfluoroalkyl group and an alkyl group in the polymer molecule. In other words, the primary chain of the fluorine-containing polymer is substituted by a perfluoroalkyl group and an alkyl group. The primary chain of the fluorine-containing polymer may be composed of one or more copolymers of organic compounds such as polyamides, polyesters, polyethers, polyols, polyolefins, polystyrenes, polyurethanes, polysulfones, vinyl resins, urea resins, phenol resins, silicon resins, acrylic resins, melamine resins, epoxy resins, polycarbonate resins, terpene resins, Shellac resins, sulfur resins, divinyl benzene/styrene copolymers, cellulose, cellulose derivatives, polysaccharides, proteins, hydrogenated proteins and the like. Preferable range of the molecular weight of the fluorine-containing polymer of compound (A) is from 500 to 2,000,000, particularly 2,000 to 500,000. It is preferred that the total number of carbon atoms in the alkyl group of the polymer (A) (hereinafter referred to as $N_H$) and the total number of carbon atoms in the perfluoroalkyl group of the polymer (A) (hereinafter referred to as $N_F$) be in the following relation: $1 \leq N_H/N_F \leq 30$. Examples of the fluorine-containing polymer include those described in Japanese patent publication Kokai Nos. 9619/1980, 29501/1980, 45756/1980, 118882/1983, 118883/1983, 59277/1983, 73712/1986 and 289009/1986. Among them, copolymers of a long-chain alkyl(meth)acrylate and (meth)acrylate bonded to fluoroalkyl obtainable according to the process described in Japanese patent publication Kokai No. 289009/1986 is preferred. For example, mention may be given to copolymers between (meth)acrylate having C16–C22 alkyl and (meth)acrylate having a C4–C36 perfluoroalkyl or polyfluoroalkyl. Examples of the alkyl(meth)acrylate having C16–C22 alkyl include esters between an alcohol such as cetyl alcohol, stearyl alcohol or behenyl alcohol and (meth)acrylic acid. Examples of the (meth)acrylate having a C4–C36 perfluoroalkyl or polyfluoroalkyl include the following compounds:

$CH_2=CHCOOC_2H_4C_6F_{13}$,
$CH_2=CHCOOC_2H_4C_8F_{17}$,
$CH_2=CHCOOC_2H_4C_{10}F_{21}$,
$CH_2=CHCOOC_2H_4C_{12}F_{25}$,
$CH_2=C(CH_3)COOC_2H_4C_6F_{13}$,
$CH_2=C(CH_3)COOC_2H_4C_{12}F_{25}$,
$CH_2=C(CH_3)COOC_2H_4C_8F_{17}$, $CH_2=CHCOOC_2H_4-(CF_2)_4-H$,
$CH_2=C(CH_3)COOC_2H_4C_{10}F_{21}$, $CH_2=CHCOOC_2H_4-(CF_2)_5-H$,
$CH_2=C(CH_3)COOC_2H_4-(CF_2)_4-H$,
$CH_2=C(CH_3)COOC_2H_4-(CF_2)_5-H$,

The proportion between the long-chain alkyl (meth-)acrylate and the (meth)acrylate having fluoroalkyl is preferably in the range from 10:1 to 1:5 (weight ratio), and more preferably from 7:1 to 1:1. It is preferred that the copolymer have the molecular weight ranging from 1,000 to 2,000,000, especially from 10,000 to 500,000 in order to secure frictional resistance and stickiness-free properties. It is also possible to use Surflon SC-101, SC-105, S-381 and S-382 (all manufactured by Asahi Glass Co.).

The fluorine-containing polymer (A) is used singly or in combination of two or more. It is preferred that the polymer component (A) be incorporated into the present detergent composition from 0.1 to 40% by weight (hereinafter referred to simply as %), and more preferably from 0.5 to 20% with respect to the total weight of the oil components in the detergent composition.

No particular limitation is imposed on the liquid oil base of the component (B) useful in the practice of this invention so far as it is in common use in cosmetic compositions and the like.

Incidentally, the term "liquid" as used herein means liquid or paste at 25° C. As examples of the liquid oil base, may be mentioned hydrocarbons, higher alcohols, higher fatty acid esters of higher alcohols, animal and vegetable oils and fats, cholesterol fatty acid esters, silicones and the like. As specific preferable examples thereof, may be mentioned liquid paraffin, squalane, polyisobutene, isopropyl parmitate, isopropyl myristate, isooctyl myristate, isotridecyl myristate, cholesteryl isostearate, dicaprylic neopentyl glycol, glyceryl tri-(2-ethylhexanoate), diglycerol 2-ethylhexanoate, hexadecyl 2-ethylhexanoate, octadecyl myristate, olive oil, jojoba oil, linear or cyclic methyl-polysiloxane, methylphenylpolysiloxane, etc.

These compounds (B) may be used either singly or in any combination thereof, and may preferably be incorporated into the present detergent composition in a range of 1-90%, particularly 30-80% based on the total weight of the detergent composition of the present invention.

The present detergent composition preferably contains various surfactants as component (C) in view of detergency and easy handling of washing off with water. As surfactants, any one of anionic, amphoteric and nonionic surfactants can be used with nonionic surfactants being particularly preferred. Examples of the nonionic surfactants include polyoxyalkylene type nonionic surfactants such as polyoxyethylene alkyl ethers, polyoxypropylene alkyl ethers, polyoxyethylene alkylphenyl ethers, polyethylene glycol fatty acid esters, ethylene oxide derivatives of propylene glycol fatty acid esters, polyoxyethylene sorbitan fatty acid esters, ethylene oxide derivatives of mono- or poly-glycerol fatty acid esters, ethylene oxide derivatives of trimethylolpropane fatty acid esters, polyoxyethylene hydrogenated castor oils, polyoxy-ethylene hydrogenated castor oil fatty acid esters, polyoxy-ethylene hydrogenated castor oil pyroglutamate and polyoxy-ethylene glycerol pyroglutamate; sucrose fatty acid esters; alkylglucosides such as decyl glucosides, dodecyl glucosides, decylpolyglucosides, dodecylpolyglucosides; polyglycerol fatty acid esters; polyglycerol alkyl ethers; and polyether modified silicones. Among these nonionic surfactants, especially preferred are polyoxyethylene alkyl ethers, polyoxyethylene fatty acid esters, polyoxyethylene sorbitan fatty acid esters, polyoxyethylene glyceryl fatty acid esters, polyoxyethylene hydrogenated castor oils and polyether modified silicones. If a gel form is desired for the present detergent composition, it is preferred to use a hydrophilic nonionic surfactant having an HLB of 9 or more.

The surfactants of the component (C) may be used either singly or in any combination thereof, and may preferably be incorporated into the present detergent composition in a range of 1-30%, particularly 5-25% based on the total weight of the detergent composition of the present invention.

The present detergent composition may take various forms such as cleansing oils, cleansing creams and cleansing gels. In the process of manufacture, water-soluble compounds having a hydroxyl group, polymers, oily ingredients which are solid at room temperature, preservatives, antioxidants, perfumes, powders, water, etc. may further be incorporated as desired.

As examples of the water-soluble compounds having a hydroxyl group useful in the practice of this invention, may be mentioned propylene glycol, isopropylene glycol, 1,3-butanediol, dipropylene glycol, glycerol, diglycerol, triglycerol, polyglycerol, trimethylolpropane, erythritol, pentaerythritol, sorbitan, sorbitol, glucose, maltitol, saccharose, trehalose, ethylene oxide or propylene oxide adducts of saccharides or sugar derivatives, polyethylene glycol, ethanol and the like. Of these, glycerol, sorbitol, maltitol, ethylene oxide adducts of sugar derivatives such as polyoxyethylene methylglucoside and ethanol are particularly preferred. These compounds may be used either singly or in any combination thereof, and may preferably be incorporated into the present detergent composition in a range of 1-50%, particularly 3-30% based on the total weight of the detergent composition of the present invention as varying depending on the intended feel upon use, viscosity of the composition and the like.

Examples of the polymer useful as an optional component of the present detergent composition include polyethylene glycol, salts of alginic acid, xanthan gum, carboxyvinyl polymer, hydroxyethylcellulose, hydroxymethylcellulose and cationic cellulose. Examples of the solid oils at room temperature include higher fatty acids, higher alcohols, glycerol fatty acid esters, polyglycerol fatty acid esters, higher fatty acid esters, cholesterol fatty acid esters and ceramide derivatives. Examples of the preservatives include alkyl ester paraoxybenzoate, sodium benzoate, potassium solbate and phenoxyethanol. Examples of the antioxidants include tocopherols.

The detergent composition according to the present invention is prepared by a method known per se by blending, and if desired with heating, the mentioned components.

The present detergent composition is very useful for removing the fluorine-containing make-up cosmetics from the surface of the skin and the hair, and in particular, from the skin. In use, the present detergent composition is first applied to the skin or the hair, and then washed away with water or tissued off. The present composition preferably contains a surfactant, which is component (C), in view that the composition can be easily removed with water and therefore refreshing feel can be provided.

According to the present invention, not only ordinary dirts of sebum and make-up cosmetics on the skin but also special dirts of fluorine-containing make-up cosmetics which are very difficult to be removed by conventional detergent compositions are quickly and efficiently removed.

The present invention will hereinafter be described more specifically by the following examples. However, it should be borne in mind that this invention is not limited to and by these examples only.

EXAMPLES 1 and 2 (Cleansing oil)

Cleansing oils of Table 3 formulations were prepared in accordance with the following procedure to evaluate their detergency on an ordinary foundation and a fluorine-containing foundation which had been applied to the skin.

(1) Preparation procedure

The components in Table 3 other than the fluorine-containing polymer were blended and heated at 70° C., where the fluorine-containing polymer was added and mixed for homogeneous solution. The obtained mixture was cooled down to room temperature to obtain a cleansing oil.

(2) Evaluation method

The ordinary foundation or the fluorine-containing foundation formulated as Table 1 were applied to the skin, a suitable amount of a cleansing oil was applied thereto and softly massaged. Subsequently, the cleansing oil was washed with water. Readiness of release of dirt when massaged and the results of removal of dirt were evaluated according to the criteria in Table 2.

TABLE 1

| Components | Fluorine-containing Foundation Proportion (%) | Ordinary Foundation Proportion (%) |
|---|---|---|
| Dimethylpolysiloxane (Shin-etsu Silicone Co., KF-96A, 6 cs) | 5 | 5 |
| Aluminum distearate | 3 | 2 |
| Squalane | — | 45 |
| Perfluoropolyether (Montefluos Co., FOMBLIN HC-04) | 45 | — |
| Dextrin fatty acid ester (Chiba Seifun K.K., Leopal KL) | 1 | 1 |
| Candelilla wax | 2.4 | 3.4 |
| Fluorine-treated titanium oxide | 10 | 10 |
| Fluorine-treated sericite | 15 | 15 |
| Fluorine-treated iron oxides (red, black & yellow) | 5 | 5 |
| Fluorine-treated mica | 7 | 7 |
| Fluorine-treated talc | 6.5 | 6.5 |

TABLE 1-continued

| Components | Fluorine-containing Foundation Proportion (%) | Ordinary Foundation Proportion (%) |
|---|---|---|
| Perfume | 0.1 | 0.1 |

Preparation: All the components other than perfume was heated at 70–100° C. to melt while stirring for homogeneous mixture, which was added with perfume and cooled down.

TABLE 2

| Rank | Release of dirt | Removal of dirt |
|---|---|---|
| 1 | Quick | Good |
| 2 | Fairly quick | Fair |
| 3 | Cannot determine | Cannot determine |
| 4 | Relatively slow | Relatively poor |
| 5 | Slow | Poor |

(3) Results

The results are shown in Table 3. The present cleansing compositions exhibited excellent detergency (release of dirt and removal of dirt) not only against the ordinary foundation but also fluorine-containing foundation.

TABLE 3

| | Invention | | Comparison | |
|---|---|---|---|---|
| Component (%) | Ex. 1 | Ex. 2 | Ex. 1 | Ex. 2 |
| Fluorine containing polymer[2] | 2 | 2 | — | — |
| Liquid paraffin | 48 | 30 | 50 | 30 |
| Dimethylpolysiloxane (5 cs) | — | 28 | — | 30 |
| Isopropyl myristate | 40 | 30 | 40 | 30 |
| Polyoxyethylene (20) Glyceryl triisostearate | 10 | 10 | 10 | 10 |
| Evaluation | | | | |
| Ordinary Foundation | | | | |
| Ready release of dirt | 2 | 1 | 2 | 1 |
| Removal of dirt | 1 | 1 | 1 | 1 |
| Fluorine-containing Foundation | | | | |
| Ready release of dirt | 1 | 1 | 4 | 4 |
| Removal of dirt | 1 | 1 | 5 | 4 |

[2]:Copolymer of stearyl methacrylate and perfluoro alkyl methacrylate (weight ratio 3/2, average MW = 90,000). Perfluoro alkyl methacrylate used: $CH_2=C(CH_3)-COOC_2H_4C_8F_{17}$

EXAMPLES 3 and 4 (O/W Cleansing cream)

Cleansing creams were prepared according to the formulations in Table 4. Similar procedure as described in Examples 1 and 2 was followed to evaluate the removal of dirt composed of a fluorine-containing foundation after the cleansing composition was washed with water.

The present cleansing compositions exhibited excellent detergency against a fluorine-containing foundation.

TABLE 4

| | Invention | | Comparison | |
|---|---|---|---|---|
| Component (%) | Ex. 3 | Ex. 4 | Ex. 3 | Ex. 4 |
| Fluorine containing polymer[2] | 2 | 2 | — | — |
| Liquid paraffin | 60 | 58 | 60 | 58 |
| Cetanol | — | 2 | — | 2 |
| Sorbitan monostearte | 3 | 3 | 3 | 3 |
| Polyoxyethylene (20) sorbitan monostearate | 3 | 3 | 3 | 3 |
| Glycerol | 10 | 10 | 10 | 10 |
| Water | ← balance → | | | |
| Removal of dirt | 1 | 1 | 4 | 4 |

[2]:Same as indicated in Table 3.

(Preparation method)

The oil components, surfactants and the fluorine-containing polymer were homogeneously blended at 70° C. to dissolve. Water was added thereto for emulsification, and cooled down to obtain a cleansing cream.

EXAMPLE 5 (W/O Cleansing cream)

| (Formulation) | |
|---|---|
| Liquid paraffin | 25% |
| Cyclic silicone (SH244, product of Toray Dow-Corning Silicone) | 25 |
| Isostearyl glyceryl ether | 2 |
| Polyether-modified silicone (SH3775C, product of Toray Dow-Corning Silicone) | 2 |
| Fluorine-containing polymer[3] | 2 |
| Glycerol | 10 |
| Water | Balance |

[3]:Copolymer of behenyl methacrylate and perfluoroalkyl methacrylate (3/1 by weight ratio, average MW = 130,000). Perfluoro alkyl methacrylate: Perfluoro alkyl methacrylate: $CH_2=C(CH_3)-COOC_2H_4C_8F_{17}$ A cleansing cream was formulated by mixing the fluorine-containing polymer, oil components and surfactants excepting the silicone at 70° C. and cooled down. Silicone was added thereto at 40° C. and cooled down to obtain a cleansing cream.

EXAMPLE 6 (Oil cleansing gel)

| (Formulation) | |
|---|---|
| Liquid paraffin | 50% |
| Cyclic silicone (SH244, product of Toray Dow-Corning Silicone) | 20 |
| Isopropyl parmitate | 15 |
| Polyoxyethylene(20)glyceryl triisostearate | 10 |
| Fluorine-containing polymer[4] | 2 |
| Aluminum diisohexadecyl phosphate | 3 |

[4]:Copolymer of stearyl acrylate and perfluoroalkyl acrylate (3/2 by weight ratio, average MW = 65,000). Perfluoroalkylacrylate: $CH_2=CH-COOC_2H_4C_8F_{17}$ An oil cleansing gel was formulated by mixing all components indicated above, and stirred for homogeneity about 5 minutes with a stirrer to obtain an oil cleansing gel.

EXAMPLE 7 (Cleansing gel)

| (Formulation) | |
|---|---|
| Liquid paraffin | 35% |
| Fluorine-containing polymer[4] | 1 |
| Polyoxyethylene(20)octyldodecyl ether | 14 |
| Sorbitol (70% solution) | 39 |
| Water | balance |

[4]:Same as Example 6.

The oil component and the fluorine-containing polymer were mixed at 70° C. for homogeneity and cooled down. The remainder components were added thereto to obtain a cleansing gel.

The cleansing compositions according to Examples 5 through 7 of the present invention are all excellent in the detergency against ordinary make-up compositions and fluorine-containing make-up compositions.

EXAMPLE 8 (Cleansing oil for tissue-off)

| (Formulation) | |
|---|---|
| Dimethylpolysiloxane (product of Shin-etsu Silicone, KF-96, 5 cs) | 48% |
| Squalane | 50 |

| (Formulation) | |
|---|---|
| Fluorine-containing polymer[5] | 2 |

[5]:Copolymer of dodecyl methacrylate, behenyl methacrylate and perfluoroalkyl methacrylate (3/3/4 by weight ratio, average MW = 74,000). Perfluoroalkylmethacrylate: $CH_2=C(CH_3)-COOC_2H_4C_8F_{17}$ The oil phase was added with the fluorine-containing polymer and stirred to dissolve.

After extending the cleansing oil for complete compatibility with an ordinary make-up composition or fluorine-containing composition, the cleansing oil was tissued off. Excellent removal of make-up dirt was obtained.

What is claimed is:

1. A detergent composition which comprises the following components (A) through (C):
   (A) from 0.1 to 40% by weight with respect to the total weight of the composition of a fluorine-containing polymer in which the primary chain is substituted by a perfluoroalkyl group and an alkyl group.
   (B) from 1 to 90% by weight with respect to the total weight of the composition of a liquid oil base, and
   (C) from 1 to 30% by weight with respect to the total weight of the composition of a surfactant.

2. The detergent composition of claim 1, is which said liquid oil base is liquid at 25° C.

3. The detergent composition of claim 1, wherein said oil base is selected from the group consisting of animal and vegetable oils and fats and cholesterol fatty acid esters.

4. The detergent composition as defined in claim 1, wherein said oil base is selected from the group consisting of hydrocarbons, higher alcohols, higher fatty acid esters of higher alcohols and silicones.

5. The detergent composition as defined in claim 1, wherein said fluorine-containing polymer has a molecular weight ranging from 500 to 2,000,000.

6. The detergent composition as defined in claim 1, wherein said fluorine-containing polymer is a copolymer of a long-chain alkyl(meth)acrylate and a (meth)acrylate containing fluoroalkyl.

7. The detergent composition as defined in claim 1, wherein said fluorine-containing polymer is a copolymer of a long-chain alkyl(meth)acrylate having an alkyl group of 16 to 22 carbon atoms and a (meth)acrylate having a perfluoro group or a polyfluoro group of 4 to 36 carbon atoms.

8. The detergent composition of claim 1, wherein said fluorine-containing polymer is present in an amount of from 0.1 to 20% by weight.

9. The detergent composition as defined in claim 1, wherein said surfactant is selected from the group consisting of anionic surfactants, amphoteric surfactants and nonionic surfactants.

10. The detergent composition as defined in claim 1, wherein said surfactant is a nonionic surfactant.

11. The detergent composition of claim 1, further comprising:
   (D) from 1 to 50% by weight of the composition of a water-soluble compound having a hydroxyl group selected from the group consisting of monoalcohols, glycols, polyglycols, glycerols, polyglycerols, saccharides and ethylene oxide adducts of saccharides.

12. A method for cleaning the face, which comprises applying, to the face, the composition as defined in claim 1.

13. A method for cleansing the skin or the hair, which comprises applying, to the skin or the hair, the composition as defined in claim 1.

14. The method of claim 13, further comprising removing said composition.

* * * * *